United States Patent [19]
Platt, Jr. et al.

[11] Patent Number: 5,669,904
[45] Date of Patent: Sep. 23, 1997

[54] SURGICAL GAS PLASMA IGNITION APPARATUS AND METHOD

[75] Inventors: Robert C. Platt, Jr.; Robin Badih Bek, both of Boulder, Colo.

[73] Assignee: Valleylab Inc., Boulder, Colo.

[21] Appl. No.: 399,682

[22] Filed: Mar. 7, 1995

[51] Int. Cl.$^6$ ............................................ A61B 17/36
[52] U.S. Cl. ............................... 606/27; 606/34; 606/39; 606/41
[58] Field of Search ...................... 606/27, 28, 32–41, 606/44–52

[56] References Cited

U.S. PATENT DOCUMENTS

| | | |
|---|---|---|
| Re. 34,432 | 11/1993 | Bertrand . |
| 3,838,242 | 9/1974 | Goucher . |
| 3,903,891 | 9/1975 | Brayshaw . |
| 3,970,088 | 7/1976 | Morrison . |
| 3,987,795 | 10/1976 | Morrison . |
| 4,040,426 | 8/1977 | Morrison et al. . |
| 4,041,952 | 8/1977 | Morrison, Jr. et al. . |
| 4,043,342 | 8/1977 | Morrison, Jr. . |
| 4,057,064 | 11/1977 | Morrison et al. . |
| 4,060,088 | 11/1977 | Morrison, Jr. et al. . |
| 4,492,231 | 1/1985 | Auth . |
| 4,781,175 | 11/1988 | McGreevy et al. . |
| 4,890,610 | 1/1990 | Kirwan, Sr. et al. . |
| 4,901,719 | 2/1990 | Trenconsky et al. . |
| 4,901,720 | 2/1990 | Bertrand . |

*Primary Examiner*—David M. Shay
*Attorney, Agent, or Firm*—Peter C. Richardson; Lawrence C. Akers; Aaron Passman

[57] ABSTRACT

An apparatus and method for igniting plasma in a surgical system is disclosed. A corona discharge is generated on a surgical handpiece which is used to ignite a plasma arc for surgical operations. The advantages include greater reliability and repeatability of plasma arc ignition. The apparatus comprises a handpiece incorporating an active electrode, a passage for ionizable gas, and a corona return electrode. The corona return electrode has a terminus on the holder and near the distal end of the holder. The corona return electrode is electrically connected to the return path of the electrosurgical generator. A non-uniform electric field is generated between the active electrode and the corona return electrode of sufficient strength so that a corona is formed near the active electrode. A separate return electrode may be on the patient, or the apparatus may be configured for bipolar electrosurgical operation by carrying the return electrode on the handpiece. A dielectric material separates the active electrode and the corona return electrode. There is substantially capacitive coupling between the active electrode and the corona return electrode. There is substantially resistive coupling between the active electrode and the return electrode.

11 Claims, 3 Drawing Sheets

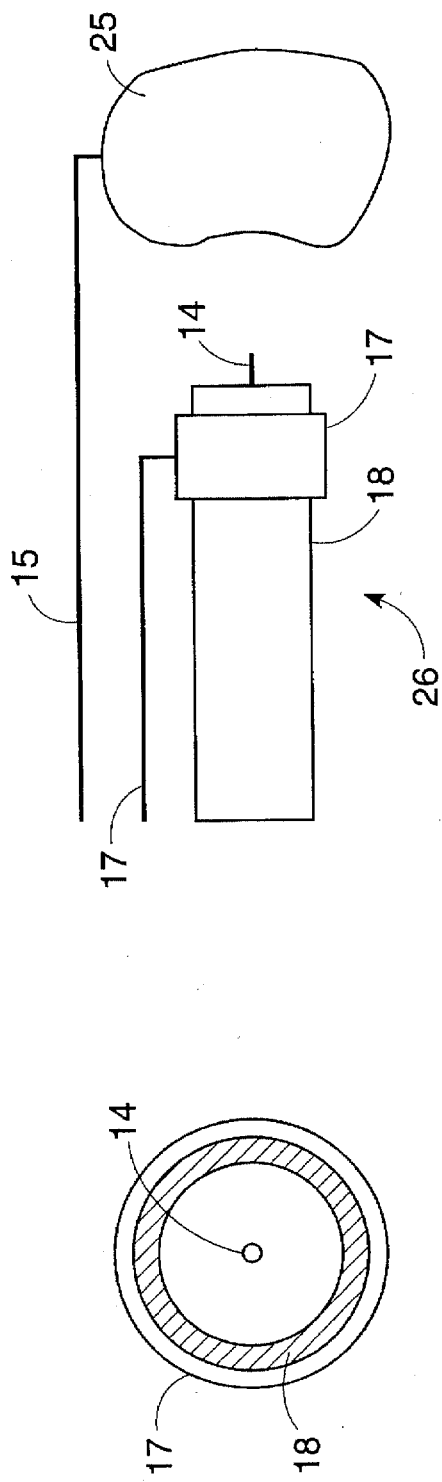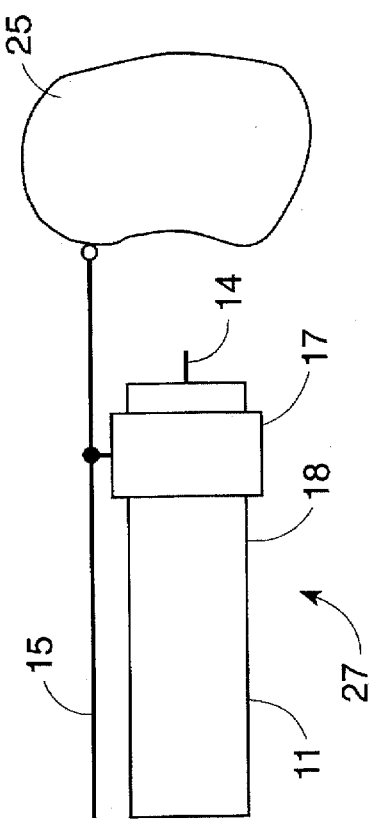

SURGICAL GAS PLASMA IGNITION APPARATUS AND METHOD

FIELD OF THE INVENTION

This invention pertains to surgical devices which incorporate electrosurgical energy and gas plasmas, and more specifically to an improved apparatus and method for igniting the plasma.

BACKGROUND OF THE DISCLOSURE

A gas plasma is an ionized gas that is capable of conducting electrical energy. Plasmas are used in surgical devices to conduct electrosurgical energy to a patient. The plasma conducts the energy by providing a pathway of low electrical resistance. The electrosurgical energy will follow this path and can therefore be used to cut, coagulate, desiccate, or fulgurate blood or tissue of the patient. One of the advantages of this procedure is that no physical contact is required between an electrode and the tissue being treated.

A plasma is created by ionizing a gas. Some electrosurgical systems have a source of regulated ionizable gas which is directed in a steady flow toward a patient. A gas that is typically used in this manner is argon, however other gasses can also be used. One advantage of having a directed flow of gas is that the plasma arc can be accurately focused and directed by the flow.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

One of the difficulties in using a plasma is its initiation. A strong electrical field is required to accelerate enough free electrons within the gas such that a cascade of ionizing collisions is initiated which creates the plasma. This is sometimes called "igniting" the plasma. Once a plasma is ignited, it may be sustained at lower electrical field potentials.

Several techniques are presently used to create strong electrical fields that can ignite the plasma. One technique is to move the tip of an electrode very close to the surgical site. The electric field along a path between an electrode and the surgical site increases as their separation decreases, and may reach a level sufficient to ignite the plasma. The drawback of this method is that a surgeon must carefully manipulate the electrode to move it close to the surgical site without actually touching the tissue. If the electrode comes in contact with the tissue it may stick, causing eschar to deposit on the electrode. During laparoscopic procedures, it is often difficult for a surgeon to sense the proximity of the electrode to the tissue.

Another technique to ignite plasma is to use a pointed electrode which will generate a stronger electrical field at the tip of the electrode. However, a pointed electrode may be undesirable if the surgeon requires a blade-shaped electrode for cutting and other tissue manipulation. Yet another technique is to provide high voltage spikes to the surgical electrode until a detector has indicated a closed circuit with the return electrode. Once a closed circuit is detected, the high voltage spikes are terminated and the electrosurgical generator returns to its normal waveform output. While this technique is effective, it requires complicated electronics and components capable of withstanding the high voltages.

U.S. Pat. No. 4,060,088 relates to an electrosurgical method and apparatus for coagulation by fulguration. The apparatus has a source of inert ionizable gas which surrounds a tubular electrosurgical electrode. A source of periodic bursts of electrosurgical energy is disclosed which is used to initiate the plasma. Also disclosed is an auxiliary discharge to aid in the initiation of the plasma, where the auxiliary discharge results from the electric field established between the doctor's finger and the active electrode.

U.S. Pat. No. 4,781,175 has an ionizable gas jet to clear bodily fluids and coagulate or achieve fulguration in the form of an improved eschar. Circuitry and computer logic are shown to control the gas jet flow and the electrosurgical energy.

U.S. Pat. No. 4,901,720 and the reissue thereof U.S. Pat. No. Re. 34,432 deal with the rate of burst energy pulses, applied to maintain leakage current within acceptable limits while having sufficient energy to initiate ionization. Circuit and logic diagrams are provided to control the burst energy by pulse width, resonance, waveform and output.

U.S. Pat. No. 4,040,426 has a method and apparatus for initiating a plasma by the use of charged particles which are generated as the inert gas flows along a tube. This charge bleeds off of the tube through inwardly pointed tips on the tube, and is used to aid in the initiation of the plasma.

U.S. Pat. No. 4,901,719 has an electrosurgical unit in combination with an ionizable gas delivery system, where there is also an improvement relating to the gas conducting means.

The disclosures of the aforesaid references are incorporated by reference and made a part hereof.

The present state of the art has not completely overcome the difficulties associated with ignition of a plasma in surgical systems. A more simple and reliable apparatus and method for igniting a plasma will make it possible for plasma-based systems, and hence surgeons, to work more effectively.

SUMMARY OF THE INVENTION

An apparatus and method for igniting plasma in a surgical system is disclosed. The advantages which can be realized by this disclosure include greater reliability and repeatability of plasma ignition. This represents a significant advance over the present state of the art because current plasma ignition techniques often require difficult manipulations by the surgeon or complicated electronics.

A basis of this disclosure is the creation and use of two different types of plasma discharges: a "corona", and a "plasma arc." The plasma arc is meant to refer to the plasma discharge that is used for surgical purposes on the patient. A corona is a low current plasma discharge that occurs around pointed or wire electrodes where the electric field is greatly enhanced. It is sometimes associated with losses in electrical power transmission. References to "plasma ignition" are to the initiation of the plasma arc. An objective of this disclosure is to generate and use the corona to aid plasma ignition.

Gas discharges operate on the principle of electron avalanche ionization of a background gas. In surgical systems, the background gas is typically argon, however other gasses are also known to be effective. The process of electron avalanche ionization is started when seed electrons are accelerated in an applied electric field to energies sufficient to ionize a gas atom or molecule upon collision. The result of the collision is an ion and two free electrons that are available to ionize two more gas atoms resulting in four free electrons, and so on.

The growth in electron density is exponential with distance traveled by the seed electrons, and a thus a plasma is generated which is capable of conducting electrical energy. This is the principle mechanism of plasma ignition. Surgical systems make use of the plasma to conduct electrosurgical energy to the tissue of a patient without having to touch the tissue with a solid electrode. The electrosurgical energy can be used to cut, coagulate, desiccate, or fulgurate the blood or tissue of the patient.

This simplified description of electron avalanche ionization neglects electron loss mechanisms. Before the plasma is ignited, the primary electron loss mechanism is through single species diffusion. The presence of electronegative atoms or molecules also is a loss mechanism. A strong electric field is required to overcome these losses. After the plasma ignites, the diffusion becomes ambipolar and the electron diffusion loss rate is reduced significantly. Thus, once the plasma is ignited, a weaker electric field can sustain the plasma arc.

For surgical systems, this means that the surgeon must have a strong electric field to ignite the plasma. In certain systems, the surgeon may see this as a requirement to move the active electrode close to the tissue of the patient, thereby generating a strong electric field. The gap between the active electrode and the tissue of the patient when the plasma finally ignites is called the "ignition gap." Once the plasma is ignited, the surgeon can sustain the arc at greater working distances than the ignition gap. This is because a weaker electric field is required to sustain the plasma arc then is required to initiate it. When low electrosurgical power is applied, the difference between the ignition gap and the working distance can be as large as an order of magnitude.

Another factor which limits the ignition of the plasma is the availability of seed electrons. The seed electrons may appear accidentally or irregularly, for example from cosmic rays. This makes the ignition of the arc an uncertain event even when the surgeon has positioned the active electrode at the proper ignition gap.

From this description of the mechanism underlying the formation of a gas plasma, it is evident that a source of free electrons would greatly facilitate electron avalanche ionization and the ignition of the plasma. The electric field required to overcome diffusion losses could be reduced, thereby increasing the ignition gap. The source of free electrons would also provide the seed electrons. The plasma would consequently ignite with greater reliability and repeatability. Thus, a source of free electrons would increase the ease and effectiveness of surgical procedures which require a plasma.

A corona is a type of discharge and hence can be a source of free electrons. The formation of a corona around an active electrode of a surgical tool will then achieve the desired objectives of increasing the ignition gap and also increasing the reliability of plasma ignition. Since coronas are low-current discharges, they consume relatively little power and so only slightly affect the power delivered to the patient. Coronas occur only in highly non-uniform electric fields generated by active and return electrodes of greatly differing sizes.

Such electric fields may be generated in an electrosurgical system by proper choice of electrode shapes and positioning. For example, a coaxial arrangement of the electrodes may be used in which the center electrode is much smaller in diameter than the coaxial outer electrode. A coaxial arrangement is one possible embodiment of this invention, however other arrangements of the electrodes can also produce the required electric field. Another possible arrangement could have a wire mesh in the handpiece and electrically connected to the return potential.

This disclosure is applicable to all electrosurgical plasma systems, including monopolar, bipolar, and sesquipolar systems. In a monopolar system, the active electrode is carried on the surgical handpiece, and the return electrode is separately attached to the patient. In bipolar and sesquipolar systems, the active and return electrodes are both carried on the surgical handpiece. This disclosure is also applicable to electrosurgical systems which have a source of regulated gas, and electrosurgical systems which are intended to ionize air.

This disclosure teaches the use of a third electrode which is called the "corona return electrode." The corona return electrode is located on the surgical handpiece and is electrically connected to the return potential of the electrosurgical generator. The corona return electrode is physically distinct from the electrosurgical return electrode, although they are both electrically in circuit with the return potential of the electrosurgical generator. A dielectric barrier is required to prevent arcing between the active electrode and the corona return electrode. The dielectric barrier may also be used to prevent arcing between the ionized gas and the corona return electrode.

A non-uniform electric field is generated between the corona return electrode and the active electrode. If sufficiently strong, this electric field causes a corona to form around the active electrode. The corona subsequently aids in the plasma ignition. A relatively small amount of current is conducted through the corona return electrode. This current is primarily the result of capacitive coupling between the active electrode and the corona return electrode.

When a surgeon is using the electrosurgical system, electrosurgical energy will travel along the active electrode, through the plasma to the patient, then to the electrosurgical return electrode, and back to the return terminal of the electrosurgical generator. In a bipolar system, the electrosurgical return electrode will be located on the handpiece, and therefore it will be necessary to ensure that the electrosurgical energy does not arc directly between the plasma and the electrosurgical return electrode. This may be accomplished either by having a dielectric barrier or by having a sufficient air gap between the plasma and the electrosurgical return electrode, or a combination of the two.

BRIEF DESCRIPTION OF THE DRAWINGS

FIG. 3 is a schematic diagram showing an end view of a holder for a monopolar electrosurgical system.

FIG. 4 is a schematic diagram showing the distal end of a holder for a monopolar electrosurgical system.

FIG. 5 is a schematic diagram showing the distal end of a holder for a bipolar electrosurgical system.

DETAILED DESCRIPTION OF THE INVENTION

Several embodiments of the plasma ignition apparatus will be described below. The basis of the ignition apparatus is the formation of a corona, which is a type of plasma discharge that is distinct from the plasma arc. In each of the embodiments, a corona return electrode is used in connection with an active electrode to create a non-uniform electric field that is conducive to the formation of a corona.

Figure 1:
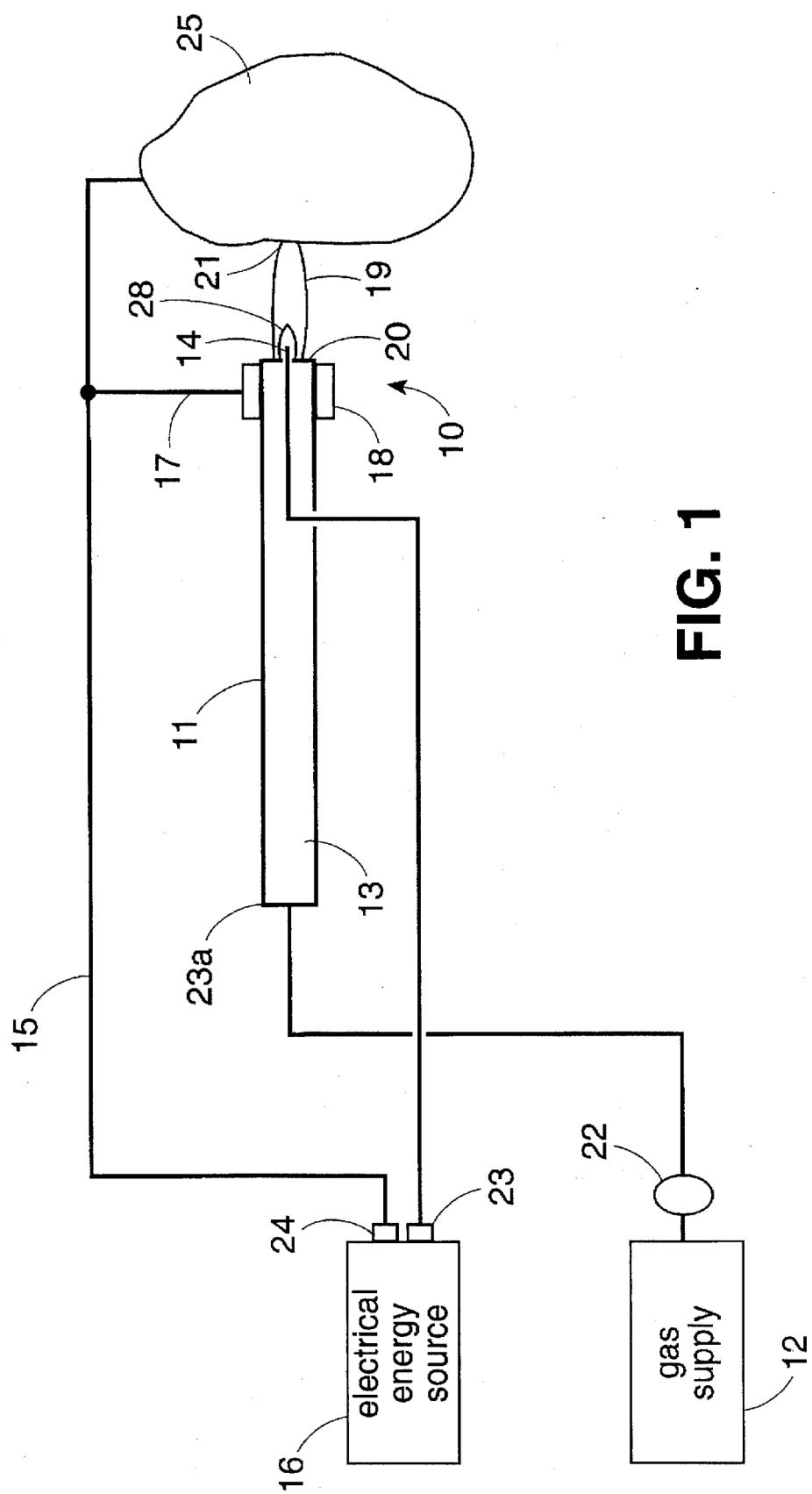
FIG. 1 is a schematic diagram of a monopolar electrosurgical system with a source of regulated gas and a gas plasma ignition apparatus.

The first embodiment of the plasma ignition system 10, as shown in FIG. 1, can be used in electrosurgical systems that have a regulated source of ionizable gas 12. The first embodiment comprises the following elements: a holder 11, a regulated source of ionizable gas 12, a passage through the holder for the gas 13, an active electrode 14, an electrical return 15, a source of high frequency electrical energy 16, a corona return electrode 17, and a dielectric member 18. The holder or handpiece 11 is for the surgeon to control during application of the plasma arc 19. The holder 11 has a distal end 20 from which the plasma arc 19 emanates. The distal end 20 of the holder 11 is directed to the surgical site 21 by the surgeon. The regulated source of ionizable gas 12 is typically a pressure vessel 12 with a gas regulator 22 attached. The ionizable gas 12 is typically argon, although other gasses, particularly the noble gasses, are known to be ionizable and may be used. A passage 13 through the holder 11 is connected at the proximal end 23 to the regulated source of ionizable gas 12, so that the gas can flow through the holder 11 and out of the holder 11 at the distal end 20.

The source of high frequency electrical energy 16 is typically an electrosurgical generator such as the Force 40, manufactured by ValleyLab, Inc., Boulder, Colo. The electrosurgical generator 16 has electrical terminals 23 and 24 of active and return potential. The active electrode 14 is electrically connected to the active terminal 23 on the electrosurgical generator 16. The active electrode 14 is placed in the passage 13 through the holder 11, so that the ionizable gas 12 will flow in contact with the active electrode 14.

An electrical return path 15 is connected to the source of high frequency electrical energy 16, and is also in circuit with the tissue or bodily fluids of the patient 25. The electrical return 15 may be attached separately to the patient 25 in a monopolar system 26, as shown in FIG. 4. Alternatively, the electrical return 15 may be on the holder 11 in a bipolar or sesquipolar system 27, as shown in FIG. 5.

In each embodiment, a corona return electrode 17 is on the holder 11 and located near the distal end 20. The corona return electrode 17 is electrically connected to the return path 15 of the electrosurgical generator 16. The function of the corona return electrode 17 is to establish a non-uniform electrical field with the active electrode 14. The non-uniform electric field will cause the formation of a corona 28 near the active electrode 14, which will thereby aid in the initiation of a surgical plasma 19.

A dielectric member 18 separates the active electrode 14 from the corona return electrode 17. There will be electrical coupling between the active electrode 14 and the corona return electrode 17, where the coupling is of a substantially capacitive nature. This will result in an electrical current in the corona return electrode 17, although the current will typically be small compared with the amount of current in the electrical return 15 when a circuit has been closed through the patient 25.

Figure 2:
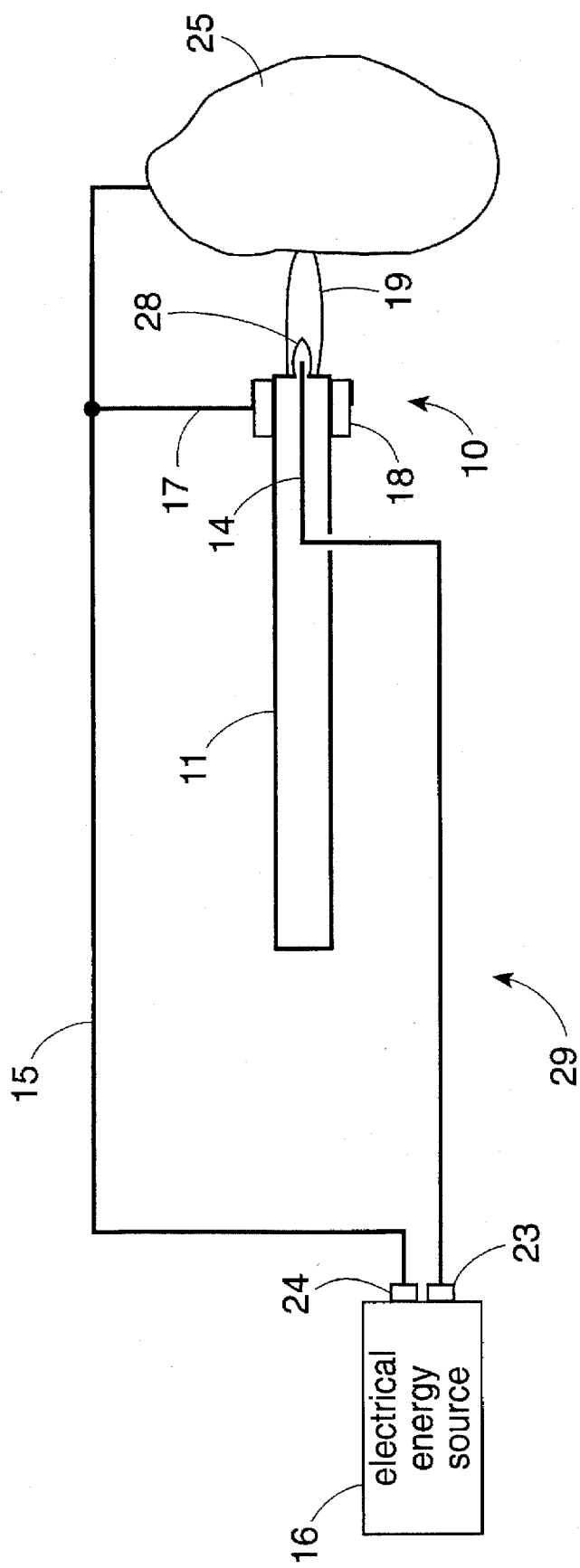
FIG. 2 is a schematic diagram of a monopolar electrosurgical system with a gas plasma ignition apparatus.

Another embodiment of the plasma ignition system 10, as shown in FIG. 2, can be used in electrosurgical systems 29 that do not have a regulated supply of ionizable gas. These systems 29 are required to ionize air in the region between the active electrode 14 and the patient 25 in order to conduct electrosurgical energy to the patient 25 without physical contact of the active electrode 14. This embodiment comprises the following elements: a holder 11, an active electrode 14, an electrical return 15, a source of high frequency electrical energy 16, a corona return electrode 17, and a dielectric member 18. This embodiment is designed to generate a non-uniform electric field between the active electrode 14 and the corona return electrode 17 so that a corona 28 will form near the active electrode 14. The corona 28 will then aid in the ionization of the air gap between the active electrode 14 and the patient 25.

There are several embodiments of the corona return electrode 17. In one embodiment, as shown in FIG. 3, the corona return electrode 17 is a conductive mesh which is disposed over the outer surface of the dielectric member 18. In another embodiment, as shown in FIG. 4, the dielectric member 18 is a tube, and the corona return electrode 17 is a thin hollow cylinder disposed over the tube 18. In yet another embodiment, the corona return electrode 17 is a conductive deposit on the outer surface of the dielectric member 18. In yet another embodiment, the corona return electrode 17 is a conductive mesh embedded in the dielectric member 18.

Skilled artisans will recognize that numerous embodiments of the corona return electrode 17 are possible. The desired objective is the production of a non-uniform electric field that has sufficient strength to generate a corona 28. Manipulation of the size, shape, and placement of the electrodes can produce the desired field characteristics.

The foregoing description of the embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application. It is to be understood that the invention can be carried out by specifically different equipment and devices, and that various modifications, both to equipment details and manufacturing methods, can be accomplished without departing from the scope of the invention itself.

What is claimed is:

1. A corona ignition system for initiating a plasma arc in an electrosurgical tool, the corona ignition system comprising:

a holder having a proximal end and a distal end;

a regulated source of ionizable gas;

a passage through the holder, forming a tube, connected proximally with the regulated source of ionizable gas so that ioniable gas may pass through the passage;

an active electrode in the passage and in contact with the regulated ionizable gas;

a source of high frequency electrical energy having first and second terminals with alternating potential thereacross, the first terminal connected to the active electrode;

a return electrode connected to the second terminal on the source of high frequency electrical energy and remote from the holder;

a corona return electrode attached to the holder and connected to the second terminal on the source of high frequency electrical energy to establish an electrical field with the active electrode;

a dielectric member located between the active electrode and corona return electrode such that the corona return electode does not protrude over the dielectric member, the dielectric member creating a high electrical impedance barrier between the active electrode and the corona return electrode to enable a corona to be created adjacent to the active electrode that can aid initiation of the plasma arc.

2. The corona ignition system of claim 1 wherein the active electrode is substantially centered within at least a portion of the passage.

3. The corona ignition system of claim 1 wherein the corona return electrode is a thin hollow cylinder.

4. The corona ignition system of claim 1 wherein the corona return electrode is at least partially in the form of a conductive mesh.

5. The corona ignition system of claim 1 wherein the corona return electrode is at least partially in the form of a conductive foil.

6. The corona ignition system of claim 1 wherein the passage is made of a dielectric material.

7. The corona ignition system of claim 6 wherein the corona return electrode is at least partially in the form of a conductive deposit on the tube.

8. The corona ignition system of claim 1 wherein the corona return electrode is a conductor supported by the passage and the corona return electrode is encased at least partially by a wall of the passage.

9. The corona ignition system of claim 6 wherein the active electrode and the passage are coaxially disposed relative to one another over at least a portion of the tube.

10. The corona ignition system of claim 1 wherein the corona return electrode is a wire attached to the holder.

11. A method of initiating a plasma arc in an electrosurgical system, the electrosurgical system comprising a generator having first and second terminals with alternating potential thereacross the electrosurgical system further comprising an active electrode, a return electrode, and a corona return electrode, the plasma arc emanating from a distal end of a holder, the method comprising the steps of:

positioning a cornea return electrode near the distal end of the holder;

positioning a dielectric barrier between the active electrode and the corona return electrode to establish a high impedance path therebetween, wherein the corona return electrode does not protrude over the dielectric barrier;

connecting the active electrode to the first terminal;

connecting the return electrode and the corona return electrode to the second terminal;

forming an electrical field between the active electrode and the corona return electrode;

generating a corona near the distal end of the holder; and initiating the plasma arc by using the corona.

* * * * *